United States Patent
Falkowski et al.

(10) Patent No.: US 11,364,479 B2
(45) Date of Patent: Jun. 21, 2022

(54) LIGAND-EXCHANGED ZEOLITE IMIDAZOLATE FRAMEWORKS

(71) Applicant: ExxonMobil Research and Engineering Company, Annandale, NJ (US)

(72) Inventors: Joseph M. Falkowski, Hampton, NJ (US); Mobae Afeworki, Phillipsburg, NJ (US); David C. Calabro, Bridgewater, NJ (US); Yi Du, Coopersburg, PA (US); Himanshu Gupta, Lebanon, NJ (US); Simon C. Weston, Annandale, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 648 days.

(21) Appl. No.: 16/287,152

(22) Filed: Feb. 27, 2019

(65) Prior Publication Data

US 2019/0282997 A1 Sep. 19, 2019

Related U.S. Application Data

(60) Provisional application No. 62/643,825, filed on Mar. 16, 2018.

(30) Foreign Application Priority Data

Mar. 20, 2018 (WO) ............... PCT/US2018/023246

(51) Int. Cl.
*B01J 20/22* (2006.01)
*B01D 53/04* (2006.01)
(Continued)

(52) U.S. Cl.
CPC ............ *B01J 20/226* (2013.01); *B01D 53/02* (2013.01); *B01D 53/04* (2013.01);
(Continued)

(58) Field of Classification Search
CPC ..... B01J 20/226; B01J 20/3085; B01D 53/04; B01D 53/02; B01D 2253/108;
(Continued)

(56) References Cited

U.S. PATENT DOCUMENTS 5,107,059 A * 4/1992 Chen ..................... C07C 7/144
 208/308
8,481,162 B2 * 7/2013 Bawendi ................ C01G 9/08
 428/403

(Continued)

FOREIGN PATENT DOCUMENTS

FR 2968656 B1 12/2012

OTHER PUBLICATIONS

Zhang et al. (Improving hydrostability of ZIF-8 membranes via surface ligand exchange, 2017, Journal of membrane science, vol. 532, pp. 1-8) (Year: 2017).*

(Continued)

*Primary Examiner* — Youngsul Jeong
(74) *Attorney, Agent, or Firm* — Robert A. Migliorini

(57) ABSTRACT

Disclosed are zeolitic imidazolate framework (ZIF) compositions in which at least a portion of the ligands in its shell have been exchanged with other ligands, and methods of making such shell-ligand-exchanged ZIFs. Also disclosed is the use of such shell-ligand-exchanged ZIFs in hydrocarbon separation processes.

5 Claims, 6 Drawing Sheets

(51) Int. Cl.
| | |
|---|---|
| *C01B 37/00* | (2006.01) |
| *B01J 20/30* | (2006.01) |
| *C01B 39/02* | (2006.01) |
| *C07C 7/13* | (2006.01) |
| *C10G 25/03* | (2006.01) |
| *B01D 53/02* | (2006.01) |
| *C10G 25/00* | (2006.01) |
| *C01B 39/00* | (2006.01) |

(52) U.S. Cl.
CPC .......... *B01J 20/3085* (2013.01); *C01B 37/00* (2013.01); *C01B 39/00* (2013.01); *C01B 39/026* (2013.01); *C07C 7/13* (2013.01); *C10G 25/003* (2013.01); *C10G 25/03* (2013.01); *B01D 2253/108* (2013.01); *B01D 2256/24* (2013.01); *B01D 2257/702* (2013.01); *C01P 2002/72* (2013.01); *C01P 2002/86* (2013.01); *C01P 2002/88* (2013.01); *C01P 2004/03* (2013.01); *C10G 2300/1081* (2013.01)

(58) Field of Classification Search
CPC .......... B01D 2256/24; B01D 2257/702; C01B 39/026; C01B 37/00; C01B 39/00
See application file for complete search history.

(56) References Cited

U.S. PATENT DOCUMENTS

| | | | |
|---|---|---|---|
| 8,636,969 | B2 | 1/2014 | Weston et al. |
| 8,907,102 | B2 | 12/2014 | Weston et al. |
| 8,920,541 | B2 | 12/2014 | Ni et al. |
| 9,919,288 | B2 | 3/2018 | Du et al. |
| 2007/0202038 | A1 | 8/2007 | Yaghi et al. |
| 2018/0001275 | A1* | 1/2018 | Jeong .................. B01D 53/228 |
| 2018/0273390 | A1 | 9/2018 | Falkowski et al. |

OTHER PUBLICATIONS

Zhang, et al. "Improving Hydrostability of ZIF-8 Membranes via Surface Ligand Exchange." Journal of Membrane Science, vol. 532, 2017, pp. 1-8.

Partial Search Report issued in related Application No. PCT/US2019/019763, dated Jun. 13, 2019 (15 pages).

Baerlocher, et al, "Atlas of Zeolite Framework Types", Elsevier, 2001, 5th Edition.

Bloch, et al, "Hydrocarbon Separations In A Metal-Organic Framework With Open Iron(II) Coordination Sites", Science, 2012, vol. 335, pp. 1606-1610.

Cravillon, et al, "Controlling Zeolitic Imidazolate Framework Nano- and Microcrystal Formation: Insight Into Crystal Growth By Time-Resolved In Situ-Static Light Scattering", Chemistry of Materials, 2011, vol. 23, pp. 210-2141.

Lalonde, et al, "Selective Solvent-Assisted Linker Exchange (SALE) in a Series of Zeolitic Imidazolate Frameworks", Inorganic Chemistry, 2015, vol. 54, pp. 7142-7144.

Liu, et al, "Improvement of Hydrothermal Stability of Zeolitic Imidazolate Frameworks", Chem. Commun., 2013, vol. 49, pp. 9140-9142.

Lovely, et al, "Oxidative Rearrangement of Imidazoles With Dimethyldioxirane" Organic Letters, 2004, vol. 6, No. 5, pp. 735-738.

Peralta, et al, "Separation of C6 Paraffins Using Zeolite Imidazolate Frameworks: Comparison With Zeolite 5A", Industrial & Engineering Chemistry Research, 2012, vol. 51, pp. 4692-4702.

Song, et al, "Transmetalations in Two Metal-Organic Frameworks of Different Framework Flexibilities: Kinetics and Core Shell Heterostructure" Crys. Eng. Comm., 2012, vol. 14, pp. 1-11.

* cited by examiner

LIGAND-EXCHANGED ZEOLITE IMIDAZOLATE FRAMEWORKS

CROSS-REFERENCE TO RELATED APPLICATIONS

This application claims priority to U.S. Provisional Application Ser. No. 62/643,825 filed Mar. 16, 2018 and PCT Application No. PCT/US2018/023246 filed Mar. 20, 2018, which is herein incorporated by reference in its entirety.

FIELD

This invention relates to zeolitic imidazolate framework (ZIF) composition in which at least a portion of the ligands in its shell have been exchanged with other ligands, and methods of making such shell-ligand-exchanged ZIFs. This invention also relates to use of such shell-ligand-exchanged ZIFs in hydrocarbon separation processes.

BACKGROUND

One known family of porous crystalline materials are zeolitic materials, which are based on the 3-dimensional, four-connected framework structure defined by corner-sharing [$TO_4$] tetrahedra, where T is any tetrahedrally coordinated cation. Among the known materials in this family are silicates that contain a three-dimensional microporous crystal framework structure of [$SiO_4$] corner sharing tetrahedral units, aluminosilicates that contain a three-dimensional microporous crystal framework structure of [$SiO_4$] and [$AlO_4$] corner sharing tetrahedral units, aluminophosphates that contain a three-dimensional microporous crystal framework structure of [$AlO_4$] and [$PO_4$] corner sharing tetrahedral units, and silicoaluminophosphates (SAPOs), in which the framework structure is composed of [$SiO_4$], [$AlO_4$] and [$PO_4$] corner sharing tetrahedral units. Included in the zeolitic family of materials are over 200 different porous framework types, many of which have great commercial value as catalysts and adsorbents.

Zeolitic imidazolate frameworks or ZIFs are a class of metal-organic frameworks that have properties similar to inorganic zeolitic materials and are composed of tetrahedrally-coordinated transition metal ions, M (e.g. Fe, Co, Cu, Zn) connected by a imidazolate-type ligand or linker moiety, IM. The angle formed by the imidazolates (IMs) when bridging the transition metals is similar to the 145° angle of the Si—O—Si bond in zeolites. ZIF counterparts of a large number of known zeolitic structures have been produced.

ZIFs have potential uses in diffusive and adsorptive separations due to their high adsorption capacity and good thermal and chemical stability. For example, ZIF-8, having a 2-methylimidizolate ligand, may be used to separate linear from branched paraffins; however, the lack of selectivity for linear vs. monobranched vs. dibranched molecules, make it difficult to obtain highly pure isomers with ZIF-8.

Therefore, there is a need to be able to tune the selectivity of high-capacity ZIF materials towards a particular type of hydrocarbon, such as, for example linear hydrocarbons. This invention meets this and other needs.

SUMMARY

Provided herein are methods for making new ZIF compositions having outermost shell ligands that have been exchanged with another ligand (i.e, shell-ligand-exchanged ZIF). These new ZIF compositions exhibit improved diffusional selectivity for particular molecular species when employed in hydrocarbon separation processes.

In one aspect, this disclosure is a method for making a shell-ligand-exchanged ZIF composition which comprises a number the steps. In step (a), a source of an initial ZIF composition is provided. The ZIF is structured as a shell which has outermost ligands of tetrahedral arrangement which comprise a general structure of $M^1$-$IM^a$-$M^2$. In this structure, $IM^a$ is an initial imidazolate ligand, and $M^1$ and $M^2$ comprise the same or different metal cations. In step (b), a source of a liquid composition is provided. The liquid composition comprises an exchange imidazolate ligand, $IM^b$, which is different from the $IM^a$ ligand. In step (c), the initial ZIF composition is contacted with the liquid composition under conditions sufficient to produce a shell-ligand-exchanged ZIF composition, where the outermost layer of ligands of tetrahedral arrangement comprise a general structure of $M^1$-$IM^a$-$IM^b$-$M^2$, wherein $IM^b$ comprises no more than 5 wt. %, preferably, less than 3 wt. % or more preferably, about 1 wt. %, based on the total weight of the shell-ligand-exchanged ZIF composition.

Conveniently, at least a portion of the outermost layer of ligands of $IM^a$ of the initial zeolitic imidazolate framework composition are exchanged or replaced with said $IM^b$. In other embodiments, at least 95% or more, preferably 97% or more, more preferably, 99% or more of the outermost layer of ligands are comprised of the exchange imidazolate, $IM^b$, based on the total weight of said shell-ligand-exchanged zeolitic imidazolate framework composition.

Conveniently, the initial zeolitic framework composition is ZIF-7 (wherein the $IM^a$ comprises benzimidazolate), or ZIF-8 (wherein $IM^a$ comprises 2-methylimidazolate), or EMM-36 (wherein $IM^a$ comprise a mixture of 4,5,6,7-tetrahydro-benzimidazolate and benzimidazolate).

Conveniently, the exchange imidazolate, $IM^b$, comprises any one of 2-methyl-imidazolate, 2-methylbenzimidazolate, 2-methyl-4,5,6,7-tetrahydrobenzimidazolate, and mixtures thereof.

Conveniently, the $M^1$ and $M^2$ are transition metals which are the same or different. Preferably, the $M^1$ and $M^2$ are both Zn.

Conveniently, the contacting step (c) of the method of this disclosure may include contacting in the presence of a solvent. The solvent is selected from the group consisting of ethanol, acetonitrile, N,N-dimethylformamide (DMF), and mixtures thereof. Preferably, the solvent is ethanol.

In another aspect, this disclosure is a shell-ligand-exchanged ZIF composition. It may be made by any one of the methods for making such shell-ligand-exchanged ZIF composition disclosed herein. When the initial ZIF is ZIF-8, the structure of shell-ligand-exchanged ZIF is: Zn-2-methylimidazolate-$IM^b$-Zn. When the initial ZIF is ZIF-7, the shell-ligand-exchanged structure is: Zn-benzimidazolate-$IM^b$-Zn. When the initial ZIF is EMM-36, the structure of the shell-ligand-exchanged ZIF is: Zn-4,5,6,7-tetrahydrobenzimidazolate and benzimidazolate-$IM^b$-Zn. For each of the shell-ligand-exchanged ZIFs, the $IM^b$ comprises or is one or more of 2-methyl-imidazolate, 2-methylbenzimidazolate, or 2-methyl-4,5,6,7-tetrahydrobenzimidazolate.

In still another aspect, this disclosure is a process for separating a hydrocarbon stream. The process comprising a number of steps. In step (a), a hydrocarbon stream which comprising a first hydrocarbon mixture and a second hydrocarbon mixture is provided. In step (b), a stream comprising a source of a shell-ligand-exchanged ZIF composition corresponding to any of the shell-ligand-exchanged ZIFs of this disclosure is provided. In step (c) the hydrocarbon stream and the stream comprising the source of the ligand-exchanged ZIF composition is contacted under suitable conditions to separate at least a portion of the first hydrocarbon mixture from the second hydrocarbon mixture.

DETAILED DESCRIPTION OF THE EMBODIMENTS

Figure 1:
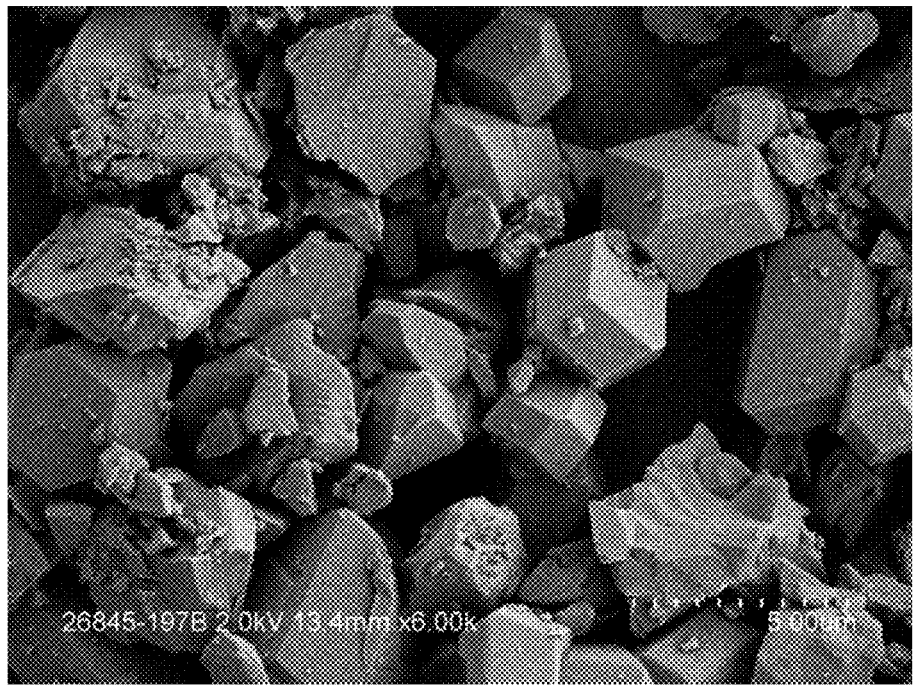
FIG. 1 shows an Scanning Electron Microscope (SEM) micrograph of the initial ZIF-8 having large crystal size particles of Example 1 before ligand treatment.

Disclosed herein are new methods for making new shell-ligand-exchanged ZIF compositions and their use in hydrocarbon separation processes. These new ZIF compositions may be described as having a tetrahedral framework comprising a general structure, $M^2$, wherein $M^1$ and $M^2$ comprises the same or different metal, and wherein IM is an imidazolate or a substituted imidazolate linking moiety.

Definitions

As used herein, the term "imidazolate" is used to describe IM, $IM^a$, and $IM^b$ herein, it is noted that, at various stages in the methods according to this disclosure, the relevant $IM/IM^a/IM^b$ may be an imidazolate (neutral charge) at particular times in the reaction sequence(s); nevertheless, the fact that these components are described using the term "imidazolate" is merely for convenience and uniformity and should be understood to encompass both situations where they are holding/delocalizing a charge and where they are neutral. In the method described herein, at least a portion of linking moiety (IM) in an existing ZIF material can be replaced or exchanged with another linking moiety by an exchange process.

As used herein, the term "IM" means an imidazolate-type ligand composition. The protonated form of this imidazolate-type ligand composition may be referred to herein as "H-IM". For the purposes of this disclosure, the term "IM" and H-IM" may be used interchangeably.

As used herein, the term "$IM^a$" means the initial organic ligand composition in the initial SIF composition of this disclosure.

As used herein, the term "$IM^b$" means the organic ligand composition used to exchange the initial, organic ligand composition, $IM^a$, that is used in the methods of this disclosure.

As used herein, the term "ZIF" means zeolitic imidazolate framework.

As used herein, the phrase "outermost layer of ligands" means those ligands located on the layer of the ZIF which is on the exterior of the layered, ZIF crystalline particle.

As used herein, the terms "ZIF-7" and "ZIF-8" means the zeolitic framework material having the SOD framework type and described in U.S. Patent Publication No. 2007/0202038 A1, published Aug. 30, 2007.

As used herein, the term "EMM-36" means the zeolitic framework material as having the SOD framework type and described in U.S. Provisional Patent Application Ser. No. 62/474,125, filed Mar. 21, 2017.

As used herein, the phrase "framework type" when used in connection with a zeolite or ZIF are the framework types as described in the "Atlas of Zeolite Framework Types," by Ch. Baerlocher, W. M. Meier and D. H. Olson (Elsevier, 5th Ed., 2001.)

Shell Ligand Exchange Method

In a step of the shell ligand exchange method described herein, an initial zeolitic imidazolate framework composition may be provided or selected. The initial zeolitic imidazolate framework (ZIF) composition may have a first organic ligand composition ($IM^a$), such as a imidazolate. The initial zeolitic framework composition is a selected from the group consisting of ZIF-7, ZIF-8, and EMM-36. In ZIF-7, the $IM^a$ comprises benzimidazolate. In ZIF-8, the $IM^a$ comprises 2-methylimidazolate. In EMM-36, the $IM^a$ comprises a mixture of 4,5,6,7-tetrahydro-benzimidazolate and benzimidazolate.

In another step of the method, a liquid composition comprising a second organic ligand composition ($IM^b$) may be provided. In the method, the $IM^b$ comprises any one of 2-methyl-imidazolate, 2-methylbenzimidazolate, 2-methyl-4,5,6,7-tetrahydrobenzimidazolate, and mixtures thereof. The second organic ligand composition may be present in a liquid composition, for example, in the form of the protonated form of the imidazolate type ligand composition and/or in the form of a salt of the imidazolate type ligand composition. The second organic ligand composition ($IM^b$) is different from the first organic ligand composition ($IM^a$). $IM^b$ may advantageously comprise a different structure or functional group than $IM^a$.

The liquid composition may comprise a solution of the second organic ligand composition ($IM^b$) and optionally, in a solvent. The solvent may be a polar organic solvent, such as N,N-dimethylformamide (DMF), N,N-diethylformamide (DEF), N,N-dimethylacetamide (DMAc), 1,3-dimethylpropyleneurea (DMPU), a sulfoxide (e.g., dimethylsulfoxide or DMSO), a phosphoramide (e.g., hexamethylphosphoramide), acetonitrile (MeCN), triethylamine (TEA), or a combination thereof. Alternatively, though not strictly organic, the solvent for the liquid composition may be an aqueous solvent, such as aqueous ammonia and ethanol, either alone or as mixtures.

In another step of the method, the initial zeolitic imidazolate framework (ZIF) composition may be contacted with the liquid composition comprising $IM^b$. This contact may take place by combining (1) the initial ZIF composition, (2) the optional solvent, and (3) a source of $IM^b$, such as H-$IM^b$, in any order. For example, the initial ZIF and H-$IM^b$ may first be combined, and the solvent may be added to this combination, accomplishing the simultaneous formation of a liquid composition comprising H-$IM^b$ and contact of this composition with ZIF. Conveniently, the source of $IM^b$ may be first dissolved in the solvent, and the resulting solution can be added to the initial ZIF. Alternatively, the $IM^b$ can be added to the ZIF and the optional solvent added thereafter to form a solution.

The weight ratio of the exchange imidizolate ligand, $IM^b$, after being contacted with the initial ZIF divided by the total weight of the shell-ligand-exchanged ZIF is in an amount of no more than 5 wt. %, preferably, no more than 3 wt. %, more preferably, no more than 2 wt. %, most preferably, no more than about 1 weight percent.

The weight ratio of the initial imidizolate ligand, $IM^a$ in the initial ZIF divided by the total weight of the shell-ligand-exchanged ZIF is in an amount of from at least about 95 up to about 99 wt. %.

The combined mixture of the initial ZIF with the liquid composition comprising $IM^b$ is maintained under conditions sufficient to achieve at least partial exchange of $IM^a$ with $IM^b$, thereby effectively converting the initial ZIF at least partially into a shell-ligand exchanged ZIF. The contact may take place for a sufficient time to achieve at least partial exchange, e.g., from at least 1 hour to as much as 10 days. The temperature of the combined mixture of the initial ZIF with the liquid composition comprising $IM^b$ may range, for example, from a temperature of about room temperature or greater, such as from about 18° C. to about 200° C. or from about 75° C. to about 150° C. or the boiling point of the solvent, if any. When the exchange of $IM^a$ with $IM^b$ is completed or substantially completed, the weight ratio of $IM^b$ to $IM^a$ may advantageously be at least 0.50, or at least 0.75, at least 0.95, or at least 1. After the initial ZIF is exchanged with $IM^b$ to form shell-ligand-exchanged ZIF, such ZIF may be recovered and treated, if necessary or desired, e.g., to remove molecules from the pore space.

$M^1$ and $M^2$ may be one or more transition metals as described for ZIFs in U.S. Patent Application Publication No. 2007/0202038. Such transition metals can include, but are not necessarily limited to, Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, and Uub.

$M^1$ and $M^2$ may additionally or alternately comprise other metals. For example, as described in U.S Patent Application Publication No. 2010/0307336, $M^1$ may be a metal having a first valency, and $M^2$ may be a metal having a second valency different from said first valency.

In one such embodiment, $M^1$ may be a monovalent metal cation, including $Li^+$, $Na^+$, $K^+$, $Cs^+$, $Rb^+$, $Cu^+$, $Ag^+$, and/or $Au^+$ (e.g., including or being $Li^+$, $Cu^+$, and/or $Ag^+$, particularly including or being $Li^+$). Additionally or alternately, in such an embodiment, $M^2$ may be a trivalent element cation, including $B^{3+}$, $Al^{3+}$, $Ga^{3+}$, $In^{3+}$, $Fe^{3+}$, $Cr^{3+}$, $Sc^{3+}$, $Y^{3+}$, and/or $La^{3+}$, wherein La is any lanthanide metal (e.g., including $B^{3+}$, $Al^{3+}$ and/or $Ga^{3+}$, particularly including $B^{3+}$).

In certain embodiments, $M^1$ and $M^2$ may both be the same. When $M^1$ and $M^2$ are both the same, they may advantageously comprise or be a transition metal, for example and preferably, Zn.

In the method for making the shell-ligand-exchanged ZIF, at least a portion of the outermost layer of ligands of $IM^a$ of said initial zeolitic imidazolate framework composition are exchanged with said $IM^b$, based on the total weight of said shell-ligand-exchanged zeolitic imidazolate framework composition.

Shell-Ligand-Exchanged ZIF

The shell-ligand-exchanged zeolitic imidazolate framework composition of this disclosure is and comprises those made by the methods disclosed herein.

When the initial zeolitic imidazolate framework composition comprises ZIF-7, the shell-ligand-exchanged ZIF composition has its outermost layer of ligands of tetrahedral arrangement which comprises a general structure of $M^1$-$IM^a$-$IM^b$-$M^2$. In this new composition, the initial imidazolate ligand from ZIF-7, $IM^a$, comprises benzimidazole. The exchange imidazolate, $IM^b$, comprises one or more of 2-methyl-imidazolate, 2-methylbenzimidazolate, or 2-methyl-4,5,6,7-tetrahydrobenzimidazolate. The transition metals, $M^1$ and/or $M^2$, may be the same or different, but comprise Zn. no more than 5 wt. % of $IM^b$, based on the total weight of said shell-ligand-exchanged zeolitic imidazolate framework composition. This shell-ligand-exchanged ZIF composition has SOD framework type.

When the initial zeolitic imidazolate framework composition comprises ZIF-8, the shell-ligand-exchanged ZIF composition has its outermost layer of ligands of tetrahedral arrangement which comprises a general structure of $M^1$-$IM^a$-$IM^b$-$M^2$. In this new composition, the initial imidazolate ligand from ZIF-8, $IM^a$, comprises 2-methylimidazolate. The exchange imidazolate, $IM^b$, comprises one or more of 2-methyl-imidazolate, 2-methylbenzimidazolate, or 2-methyl-4,5,6,7-tetrahydrobenzimidazolate. The transition metals, $M^1$ and/or $M^2$, may be the same or different, but comprise Zn. no more than 5 wt. % of $IM^b$, based on the total weight of said shell-ligand-exchanged zeolitic imidazolate framework composition. This shell-ligand-exchanged ZIF composition has SOD framework type.

When the initial zeolitic imidazolate framework composition comprises EMM-36, the shell-ligand-exchanged ZIF composition has its outermost layer of ligands of tetrahedral arrangement which comprises a general structure of $M^1$-$IM^a$-$IM^b$-$M^2$. In this new composition, the initial imidazolate ligand from EMM-36, $IM^a$, comprises a mixture of 4,5,6,7-tetrahydrobenzimidazolate and benzimidazolate. The exchange imidazolate, $IM^b$, comprises one or more of 2-methyl-imidazolate, 2-methylbenzimidazolate, or 2-methyl-4,5,6,7-tetrahydrobenzimidazolate. The transition metals, $M^1$ and/or $M^2$, may be the same or different, but comprise Zn. no more than 5 wt. % of $IM^b$, based on the total weight of said shell-ligand-exchanged zeolitic imidazolate framework composition. This shell-ligand-exchanged ZIF composition has SOD framework type.

In any of the shell-ligand exchanged ZIF compositions herein, the weight ratio of the exchange imidizolate ligand, $IM^b$, after being contacted with the initial ZIF divided by the total weight of the shell-ligand-exchanged ZIF is in an amount of no more than 5 wt. %, preferably, no more than 3 wt. %, more preferably, no more than 2 wt. %, most preferably, no more than about 1 weight percent. The weight ratio of the initial imidizolate ligand, $IM^a$ in the initial ZIF divided by the total weight of the shell-ligand-exchanged ZIF is in an amount of from at least about 95 up to about 99 wt. %.

Use of Shell-Ligand-Exchanged ZIF in Hydrocarbon Separation

The shell-ligand-exchanged ZIF may be used in a process for separating a hydrocarbon stream. In the first step of this process, a hydrocarbon stream is provided. The hydrocarbon stream may comprise a first hydrocarbon mixture and a second hydrocarbon mixture. In one embodiment, the first hydrocarbon mixture may a linear paraffin, such as an alkane, for example, pentane, hexane and the like. The second hydrocarbon mixture may be a branched paraffin, such as an isoalkane, for example, iso-pentane or methylpentane, and the like.

In the second step, a stream comprising a source of a shell-ligand-exchanged zeolitic imidazolate framework composition disclosed herein or made by one of the methods of this disclosure.

In the third step, the hydrocarbon stream and the stream comprising said source of the shell-ligand-exchanged ZIF composition under suitable conditions to separate at least a portion of said first hydrocarbon mixture from said second hydrocarbon mixture.

EXAMPLES

The invention will now be more particularly described with reference to the following non-limiting Examples and the accompanying drawings.

In the Examples, all chemicals used in the treatment and analysis of materials were commercial grade and purchased from Sigma-Aldrich, except for 2-methyl-4,5,6,7-tetrahydrobenzimidazolate, a solid, made according to reference Lovely, C. J.; Du, H.; He, Y.; Dias, H. V. R. "Oxidative Rearrangment of Imidazolates with Dimethyldioxirane" Org. Lett. 2004, 6, 735-738). All chemicals were handled in air.

The large crystal size particle, 3-5 μm (micron), ZIF-8, in the activated form (i.e., with solvent molecules substantially removed), was prepared as described in Cravillon, J.; Nayuk, R.; Springer, S.; Feldhoff, A.; Huber, K.; Wiebcke M. Chem. Mater. 2011, 23, 2130-2141. The small crystal size particle, 200-500 nm (nanometer), ZIF-8, in activated form was commercially-available BASOLITE' Z1200, obtained from Sigma Aldrich. Activated ZIF-8 is believed to be highly hydrophobic solids, and thus were stored under ambient condition and handled in air. ZIF-8 is a material having the empirical formula Zn(2-methyl imidazolate)$_2$ and has the structure framework type of SOD.

Figure 2:
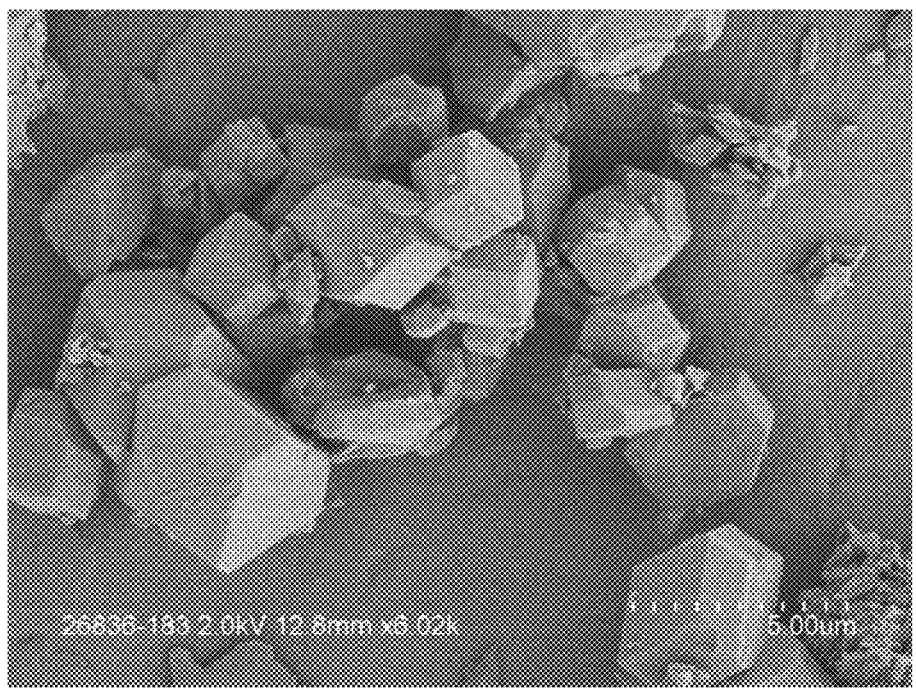
FIG. 2 shows an SEM micrograph of ZIF-8 having large crystal size particles of Example 1 after treatment with 2Me-4HBIM ligand.
Figure 3:
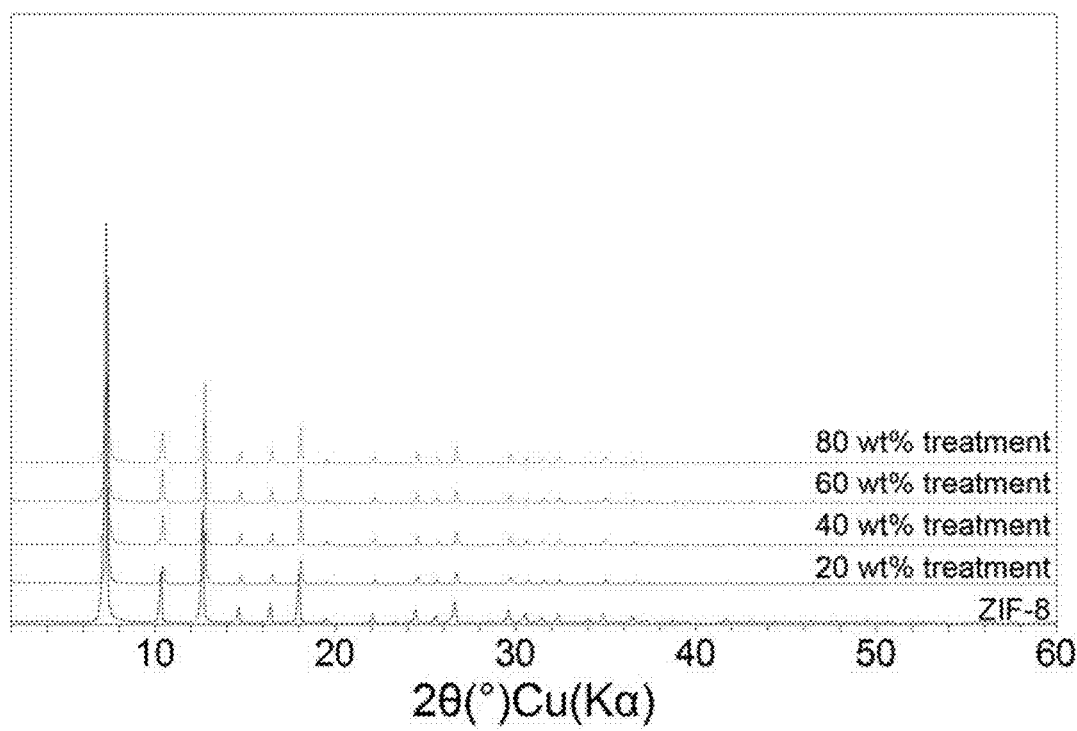
FIG. 3 shows an X-ray diffraction (XRD) patterns of ZIF-8 having large crystal size particles after treatment with differing amounts of 2Me-4HBIM ligand.
Figure 4:
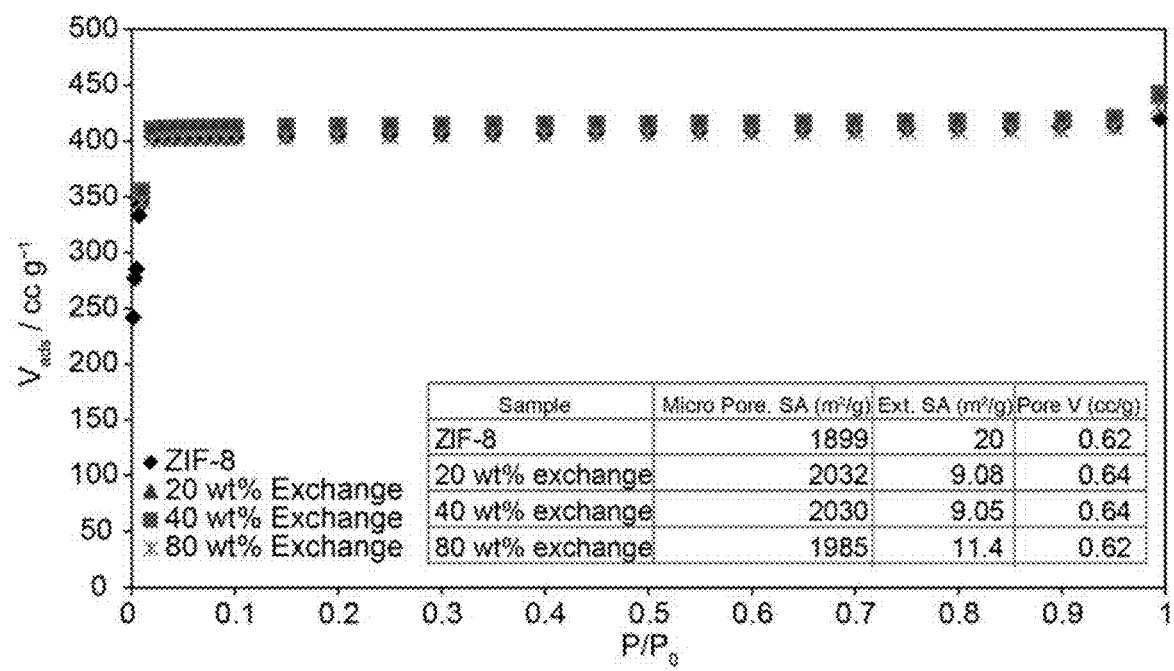
FIG. 4 shows nitrogen (N2) sorption isotherms of ZIF-8 having large crystal size particles after treatment with differing amounts of 2Me-4HBIM.

Example 1: Surface Treatment of Large (3-5 μm) Crystal Size Particles of ZIF-8 with 2-methyl-4,5,6,7-tetrahydrobenzimidazolate About 200 mg of ZIF-8 having large crystal size particles, 3 to 5 μm (micron), prepared as described above, was suspended in 10 mL of ethanol. To this suspension, 2-methyl-4,5,6,7-tetrahydrobenzimidazolate (2Me 4HBIM) was added (between 40 and 200 mg corresponding to 20 wt. %, 25 wt. %, 40 wt. %, 60 wt. %, 80 wt. % and 100 wt. %, respectively). The reaction was allowed to stir at 60° C. overnight. The following day, the slurry was filtered and the solids were washed with ethanol and dried at 90° C. under air to produce the surface-treated ZIF-8 material. SEM micrographs (SEM) both before and after treatment in FIG. 1 and FIG. 2 show little difference in the crystalline particles. FIG. 1 shows the SEM micrograph of the large crystal ZIF-8 starting material. FIG. 2 shows the SEM of large-crystal ZIF-8 after surface treatment with 2-methyl-4,5,6,7-tetrahydrobenzimidazolate. The X-ray powder diffraction (XRD) patterns of large-crystal ZIF-8 treated with differing amounts (20 wt. % to 80 wt. %) of 2Me 4HBIM is shown in FIG. 3. The XRD patterns indicate that the crystalline and microporous structure are unchanged during this treatment. The nitrogen (N2) sorption isotherms of the initial large-crystal ZIF-8 material as well as materials after treatment with 20 wt. %, 450 wt. %, 75 wt. %, or 100 wt. % of 2Me-4HBIM are shown in FIG. 4. The N2 sorption isotherms are nearly identical and also indicate that the internal porosity is unchanged during this treatment, as evident by similar surface area and t-plot pore volume, as evident by similar surface area and t-plot pore volume.

Examples 2 to 4: Surface Treatment of Large (3-5 μm) Particles of ZIF-8 with 2-methylimidazolate, 2-methylbenzimidazolate and 4,5,6,7-tetrahydrobenzimidazolate The procedure of Example 1 was repeated, except that the large crystal, 3-5 μm sized, ZIF-8 was treated with 2-methylimidazolate, 2-methylbenzimidazolate and 4,5,6,7-tetrahydrobenzimidazolate.

Example 5: Surface Treatment of Small (200-500 nm sized) Crystals of ZIF-8 with 2-methyl-4,5,6,7-tetrahydrobenzimidazolate The procedure of Example 1 was repeated, except that the ZIF-8 material was a small crystal, 200-500 nm (nanometer) sized, ZIF-8 which was also treated with 2-methyl-4,5,6,7-tetrahydrobenzimidazolate.

Figure 5:
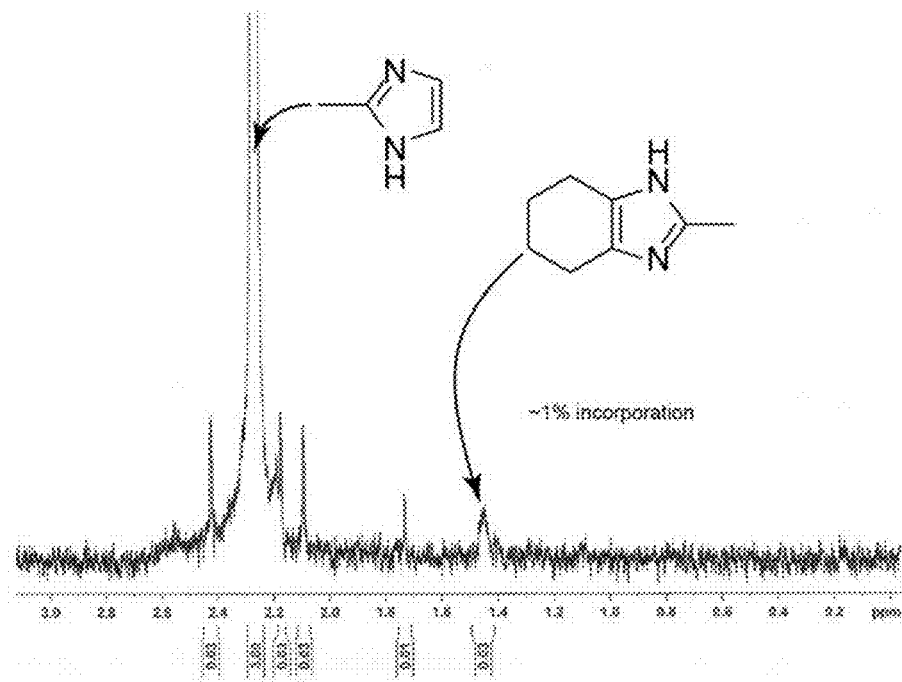
FIG. 5 shows the $^1$H Nuclear Magnetic Resonance (NMR) peaks for ZIF-8 having small crystal size particles (BASOLITE Z1200™) of Example 4 after treatment with differing amounts of 2Me-4HBIM ligand.

To establish the extent of ligand exchange, the materials were digested in dilute DCl/D$_2$O and analyzed by $^1$H NMR spectroscopy. FIG. 5 shows $^1$H NMR spectra of surface-treated BASOLITE™ Z1200 crystals after treatment with 100 wt. % of 2Me-4HBIM. The spectrum indicates that only about 1% of the material is actually the surface-bound ligand comprise 2Me-4HBIM.

Figure 6:
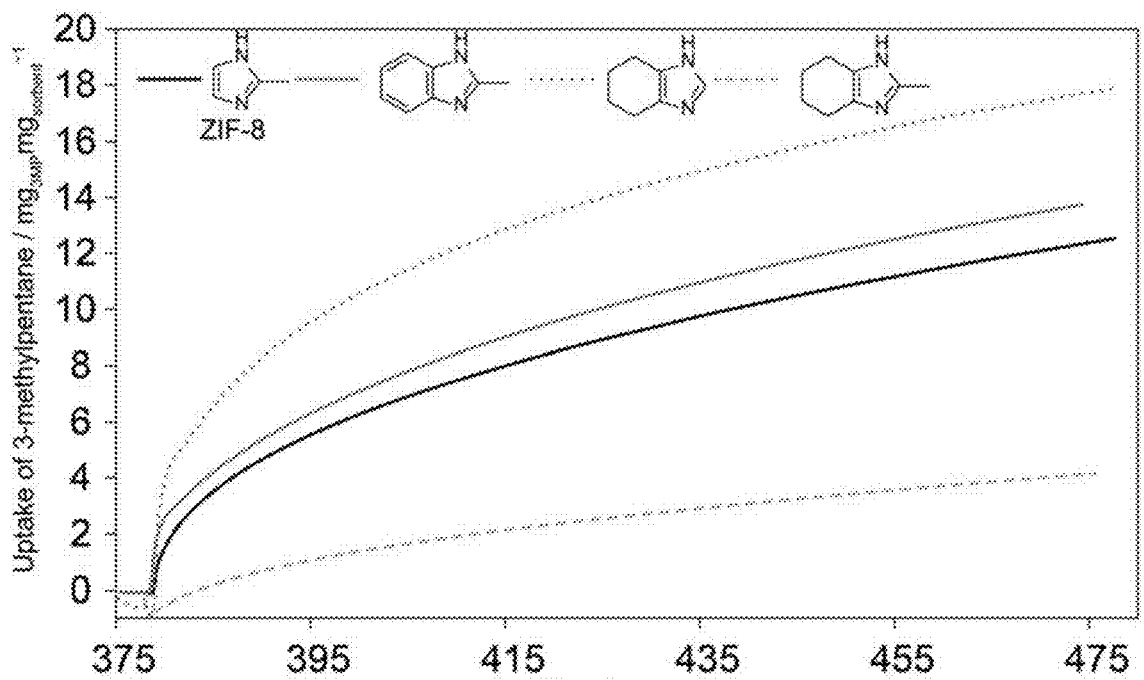
FIG. 6 shows thermogravimetric analysis (TGA) uptake curves for 3-methylpentane for ZIF-8 having large crystal size particles after treatment with 2-methylimidazolate, 2-methylbenzimidazolate, 4-tetrahydrobenzimidazolate and 2Me-4HBIM ligands.

Example 6: Paraffin Diffusivity Evaluation—Treated ZIF-8 Large (3-5 μm) Particles To probe the effect of the surface exchange on the diffusivity of paraffin molecules into the surface-treated ZIF-8 material of Examples 1-4, these materials were subjected to gas streams containing a partial pressure of 75 Torr of 3-methylpentane at 125° C. FIG. 6 shows the TGA (thermogravimetric analysis) uptake curves of 3-methylpentane into surface treated, large-crystal ZIF-8 of Examples 1-4 after treatment with different ligands (i.e., 2-methylimidazolate, 2-methylbenzimidazolate and 4,5,6,7-tetrahydrobenzimidazolate and 2-methyl-4,5,6,7-tetrahydrobenzimidazolate). Surprisingly, it was observed that, of the surface treatments investigated, only 2Me-4HBIM produced a material with hindered 3-methylpentane diffusivity. Exchanges attempted with 2-methylimidazolate and 2-methylbenzimidazolate show similar uptake rates while 4,5,6,7-tetrahydrobenzimidazolate actually shows increases in diffusivity compared to the untreated ZIF-8 basecase.

Figure 8:
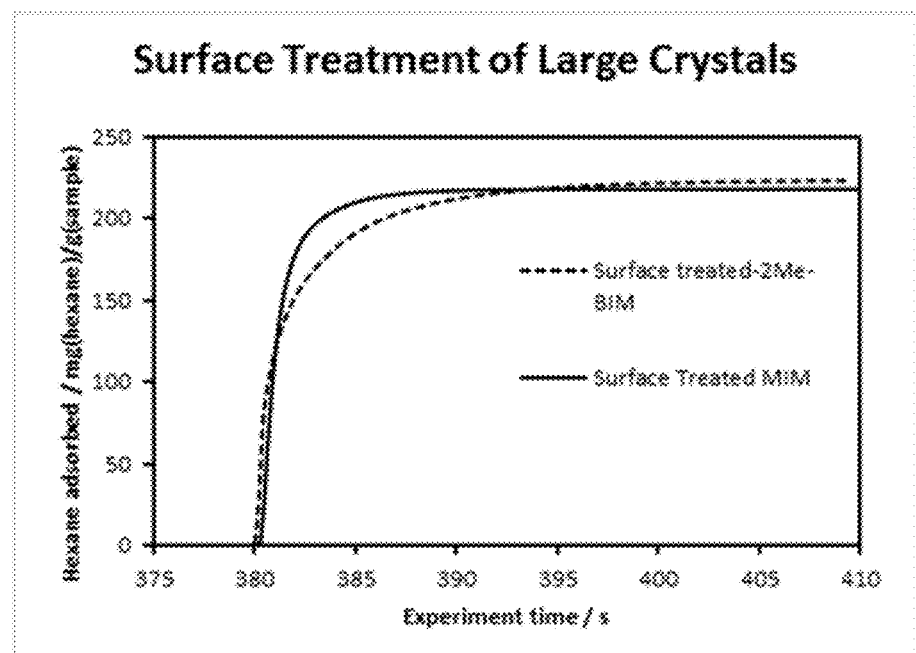
FIG. 8 shows hexane uptake curves for ZIF-8 having large crystal size particles after treatment with 2Me-4HBIM ligand and after treatment with methyl imidazolate (MIM) as a control under identical conditions for comparison.

The TGA of the uptake of n-hexane for large crystal ZIF-8 after treatment with 2Me-4HBIM (Example 1) was compared under identical conditions to large crystal ZIF-8 after treatment with 2-methyl imidazolate (Example 2) as a control, as shown in FIG. 8. As can be seen, it is the organic specifically that is affecting diffusion, and not the treatment conditions, such as heating any imidazolate in ethanol.

Figure 7:
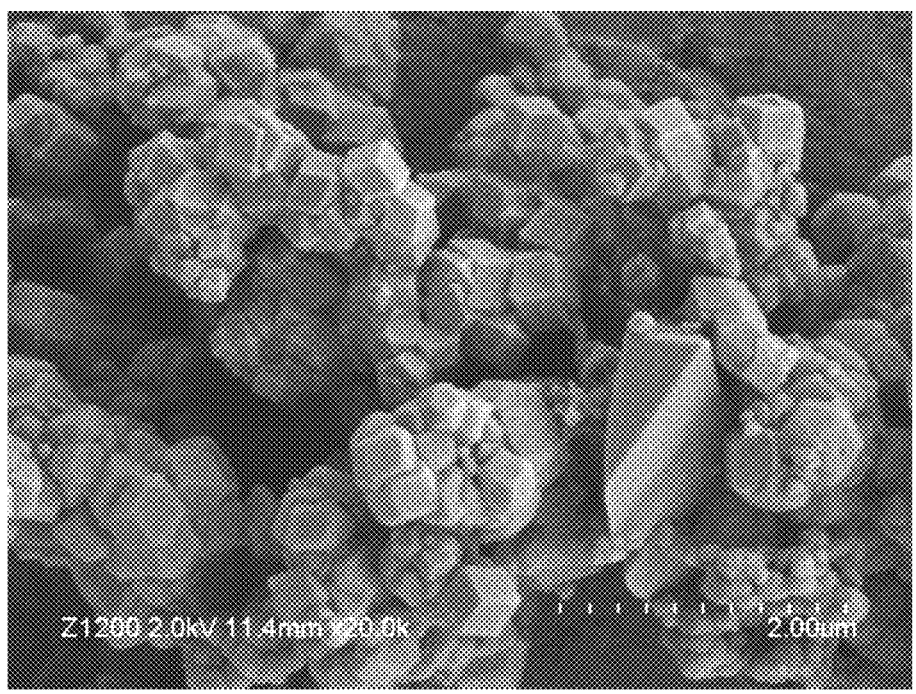
FIG. 7 shows an SEM micrograph of the initial ZIF-8 (Basolite Z1200) having small crystal size particles before ligand treatment.
Figure 9A:
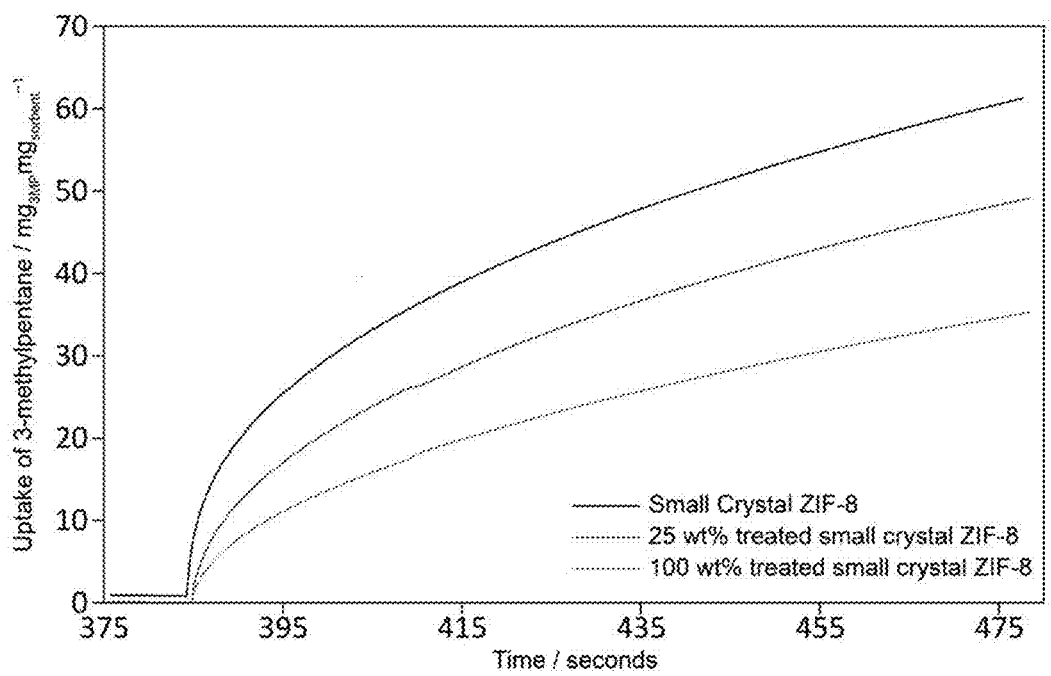
FIG. 9A shows TGA uptake curves of 3-methylpentane into small-crystal size particles of ZIF-8 after treatment with different amounts of 2Me-4HBIM.
Figure 9B:
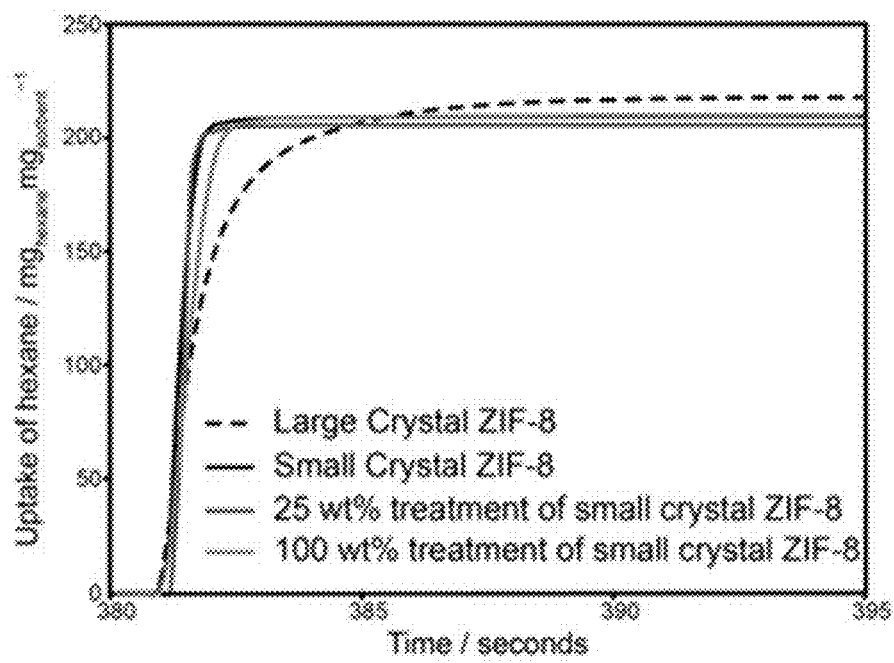
FIG. 9B shows TGA uptake curves of n-hexane into large-crystal size and small-crystal size particles of ZIF-8 after treatment with different amounts of 2Me-4HBIM.

Example 7: Paraffin Diffusivity Evaluation—Treated ZIF-8 Small (200-500 nm) Crystals To demonstrate that this effect is not a crystal size effect, a small crystal size ZIF-8, having 200-500 nm crystals obtained from Sigma Aldrich. FIG. 7 shows the SEM of ZIF-8 (BASOLITE™ Z1200) crystals obtained from Sigma Aldrich before treatment. These small crystal size ZIF-8 materials were treated with 2Me-4HBIM and tested by both 3-methylpentane uptake as well as n-hexane uptake. FIG. 9A shows the TGA uptake curves of 3-methylpentane into surface treated, small-crystal ZIF-8 after treatment with different amounts of 2Me-4HBIM. As can be seen in FIG. 9A, there is a similar decrease in the rate of 3-methylpentane uptake upon treatment of small crystal ZIF-8 with 2Me-4HBIM as there was with large crystal ZIF-8 treated with 2Me-4HBIM. FIG. 9B shows the TGA uptake curves of n-hexane into small-crystal ZIF-8 as compared to large crystal ZIF-8 after treatment with different amounts of 2Me-4HBIM. As can be seen, there is no meaningful decrease in hexane adsorption results.

The results of Examples 6 and 7 are summarized in Table 1 for surface treated 3-5 µm (micron) large crystal ZIF-8, and in Table 2 for surface treated 200-500 nm (nanometer) small crystal ZIF-8.

TABLE 1

Surface Treated (3-5 µm) ZIF-8 Particles

| Example | 2Me-4HBIM | 2Me-IM | 2Me-BIM | 4HBIM | 3-Me-$C_5$ Uptake |
|---|---|---|---|---|---|
| 1 | Yes | | | | Decrease |
| 2 | | Yes | | | No Change |
| 3 | | | Yes | | No Change |
| 4 | | | | Yes | Increase |

TABLE 2

Surface Treated (200-500 nm) ZIF-8 Crystals

| Example | 2Me-4HBIM | 3-Me-$C_5$ Uptake | n-$C_6$ Uptake |
|---|---|---|---|
| 5 | Yes | Decrease | No Change |

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The invention claimed is:

1. A shell-ligand-exchanged zeolitic imidazolate framework composition comprising:
    a zeolitic imidazolate framework composition comprising ZIF-8 and having outermost layer of ligands of tetrahedral arrangement which comprises a general structure of $M^1$-$IM^a$-$IM^b$-$M^2$ and no more than 5 wt. % of $IM^b$, based on a total weight of said shell-ligand-exchanged zeolitic imidazolate framework composition,
    wherein said:
        (i) $IM^a$ comprises 2-methyl-imidazolate,
        (ii) $IM^b$ comprises 2-methyl 4,5,6,7-tetrahydrobenzimidazolate, and
        (iii) $M^1$ and/or $M^2$ comprise Zn.

2. A shell-ligand-exchanged zeolitic imidazolate framework composition comprising:
    a zeolitic imidazolate framework composition comprising ZIF-7 and having outermost layer of ligands of tetrahedral arrangement which comprises a general structure of $M^1$-$IM^a$-$IM^b$-$M^2$, and no more than 5 wt. % of $IM^b$, based on a total weight of said shell-ligand-exchanged zeolitic imidazolate framework composition,
    wherein said:
        (i) $IM^a$ comprises benzimidazolate,
        (ii) $IM^b$ comprises one or more of 2-methyl-imidazolate, 2-methylbenzimidazolate, or 2-methyl-4,5,6,7-tetrahydrobenzimidazolate,
        (iii) $M^1$ and/or $M^2$ comprises Zn.

3. A shell-ligand-exchanged zeolitic imidazolate framework composition comprising:
    a zeolitic imidazolate framework composition comprising EMM-36 and having outermost layer of ligands of tetrahedral arrangement which comprises a general structure of $M^1$-$IM^a$-$IM^b$-$M^2$, and no more than 5 wt. % of $IM^b$, based on a total weight of said shell-ligand-exchanged zeolitic imidazolate framework composition,
    wherein said:
        (i) $IM^a$ is a mixture of 4,5,6,7-tetrahydrobenzimidazolate and benzimidazolate,
        (ii) $IM^b$ comprises one or more of 2-methyl-imidazolate, 2-methylbenzimidazolate, or 2-methyl-4,5,6,7-tetrahydrobenzimidazolate, and
        (iii) $M^1$ and said $M^2$ are both Zn.

4. A process for separating a hydrocarbon stream, the process comprising the steps of:
    (a) providing a hydrocarbon stream comprising a first hydrocarbon mixture and a second hydrocarbon mixture;
    (b) providing a stream comprising a source of a shell-ligand-exchanged zeolitic imidazolate framework composition corresponding to any one of claims 1 to 3;

(c) contacting said hydrocarbon stream and said stream comprising said source of said shell-ligand-exchanged zeolitic imidazolate framework composition under suitable conditions to separate at least a portion of said first hydrocarbon mixture from said second hydrocarbon mixture.

5. The process of claim 4, wherein said first hydrocarbon mixture comprises linear hydrocarbon paraffins and said second hydrocarbon mixture comprises branched hydrocarbon paraffins.

* * * * *